US00PP28087P3

(12) United States Plant Patent
Hoogendoorn

(10) Patent No.: US PP28,087 P3
(45) Date of Patent: Jun. 6, 2017

(54) ***ONCIDIUM* ORCHID PLANT NAMED 'ONCDBALCOJ'**

(50) Latin Name: ***Oncidium altissimum* Sw.**
Varietal Denomination: ONCDBALCOJ

(71) Applicant: ANTHURA B.V., Bleiswijk (NL)

(72) Inventor: Gert-Jan Hoogendoorn, Woubrugge (NL)

(73) Assignee: ANTHURA B.V., Bleiswijk (NL)

( * ) Notice: Subject to any disclaimer, the term of this patent is extended or adjusted under 35 U.S.C. 154(b) by 79 days.

(21) Appl. No.: 14/545,660

(22) Filed: Jun. 3, 2015

(65) Prior Publication Data

US 2016/0360674 P1 Dec. 8, 2016

(51) Int. Cl.
*A01H 5/02* (2006.01)

(52) U.S. Cl.
USPC ..... Plt./311

(58) Field of Classification Search
USPC ..... Plt./311
See application file for complete search history.

(56) References Cited

PUBLICATIONS

Upov Pluto Plant Variety Database Sep. 24, 2016 retrieved on Sep. 29, 2016, retrieved from the Internet at <https://www3.wipo.int/pluto/user/en/index.jsp> one page.*
EU Community Plant Variety Rights Application No. 2014/2611, Application No. A201405235, filed Oct. 27, 2014, 7 pages.
EU Community Plant Variety Office Official Gazette, Jun. 2014, Dec. 15, 2014, cover page and pp. 35, 56.

* cited by examiner

*Primary Examiner* — June Hwu
(74) *Attorney, Agent, or Firm* — Jondle & Associates, P.C.

(57) ABSTRACT

A new and distinct variety of *Oncidium* plant named 'ONCDBALCOJ', particularly characterized by having yellow flowers with a light brown spot in the area of the callus and striations on the sepals and petals, 1-3 peduncles, a peduncle that is short and moderate, leaves that are lanceolate and moderately elongated, and is propagated by tissue culture is disclosed.

3 Drawing Sheets

Genus and species: *Oncidium altissimum* Sw.
Variety denomination: 'ONCDBALCOJ'.

BACKGROUND OF THE NEW PLANT

The present invention comprises a new and distinct cultivar of *Oncidium* plant, botanically known as *Oncidium altissimum* Sw. of the Orchidaceae family, and hereinafter referred to by the cultivar name 'ONCDBALCOJ'.

*Oncidium* comprises a genus of about 330 species of herbaceous perennials many of which, or the hybrids thereof, are suitable for cultivation at the home or greenhouse. *Oncidium* thrives growing as lithophytes or terrestrials and is distributed throughout the American tropics and extending into South-Central America. All *Oncidium* exhibit a sympodial growth habit. The species typically have 4 leaves per mature pseudobulb: 2 lanceolate leaves with acute apex grown on the apex of the pseudobulb and 2 leaves grown from the axis at the base (sympodial growth). The peduncles vary in size from 20 to over 60 cm.

*Oncidium* orchids in the horticultural trade are frequently used to furnish cut flowers for the florist trade or sold as flowering potted plants for home or interiorscape.

*Oncidium* produces upright or pendent lateral racemes to panicles, often with many showy flowers which open in succession beginning with the lowermost. The flowers possess three sepals and two petals; the lateral ones being alike. The lowermost petals, called the labellum, are three-lobed and are often more brightly-colored than the other flower segments. Flower colors include various shades of pink, white, yellow, and red-brown.

*Oncidium* orchids are typically propagated from seeds. Asexual propagation of *Oncidium* is often done from offshoots which arise from the lower bracts of the inflorescence. The resulting plants are detached from the mother plants and may be planted in a suitable substrate.

The new *Oncidium* 'ONCDBALCOJ' is particularly characterized by its attractive and unique, yellow flowers with a light brown spot in the area of the callus and striations on the sepals and petals, a short and compact plant habit, economical propagation by tissue culture, rapid growth, and a plant dimension suitable for packaging and shipping to the market.

'ONCDBALCOJ' is a product of a planned breeding program conducted by the inventor Gert-Jan Hoogendoorn, in Bleiswijk, The Netherlands.

The new *Oncidium* 'ONCDBALCOJ' originated from a cross made by the inventor in August 2008 in Bleiswijk, The Netherlands. The female parent is a yellow *Oncidium* pot plant named '60000-0041' (unpatented) and the male parent is a yellow *Oncidium* pot plant named '60000-0522' (unpatented). A single plant was selected in August 2011 and has been asexually reproduced repeatedly by meristem tissue culture in Bleiswijk, The Netherlands over a 2.5 year period. The new variety has been found to retain its distinctive characteristics through successive asexual propagations.

Asexual reproduction of 'ONCDBALCOJ' by tissue culture was first performed in September 2012 in Bleiswijk, The Netherlands and has demonstrated that the new cultivar is firmly fixed and retained through successive generations of asexual reproduction.

Plant Breeder's Rights for this variety have been applied for in Europe on Oct. 27, 2014. 'ONCDBALCOJ' has not been made publicly available or sold anywhere in the world more than one year prior to the filing date of this application.

SUMMARY OF THE INVENTION

The following are the most outstanding and distinguishing characteristics of this new cultivar when grown under normal horticultural practices in Bleiswijk, The Netherlands.

1) Yellow flowers with light brown spot in area of callus and striations on the sepals and petals;
2) 1-3 peduncles;
3) Peduncle is short and moderate;
4) The shape of the leaf is lanceolate and moderately elongated; and
5) Plants are propagated by meristem tissue culture.

DESCRIPTION OF THE PHOTOGRAPHS

This new *Oncidium* plant is illustrated by the accompanying photographs which show the overall plant habit including blooms and foliage of the plant; the colors shown are as true as can be reasonably obtained by conventional photographic procedures. The photographs are of a 40-week old plant grown in a greenhouse in Bleiswijk, The Netherlands in December 2014.

DESCRIPTION OF THE NEW VARIETY

Figure 1:
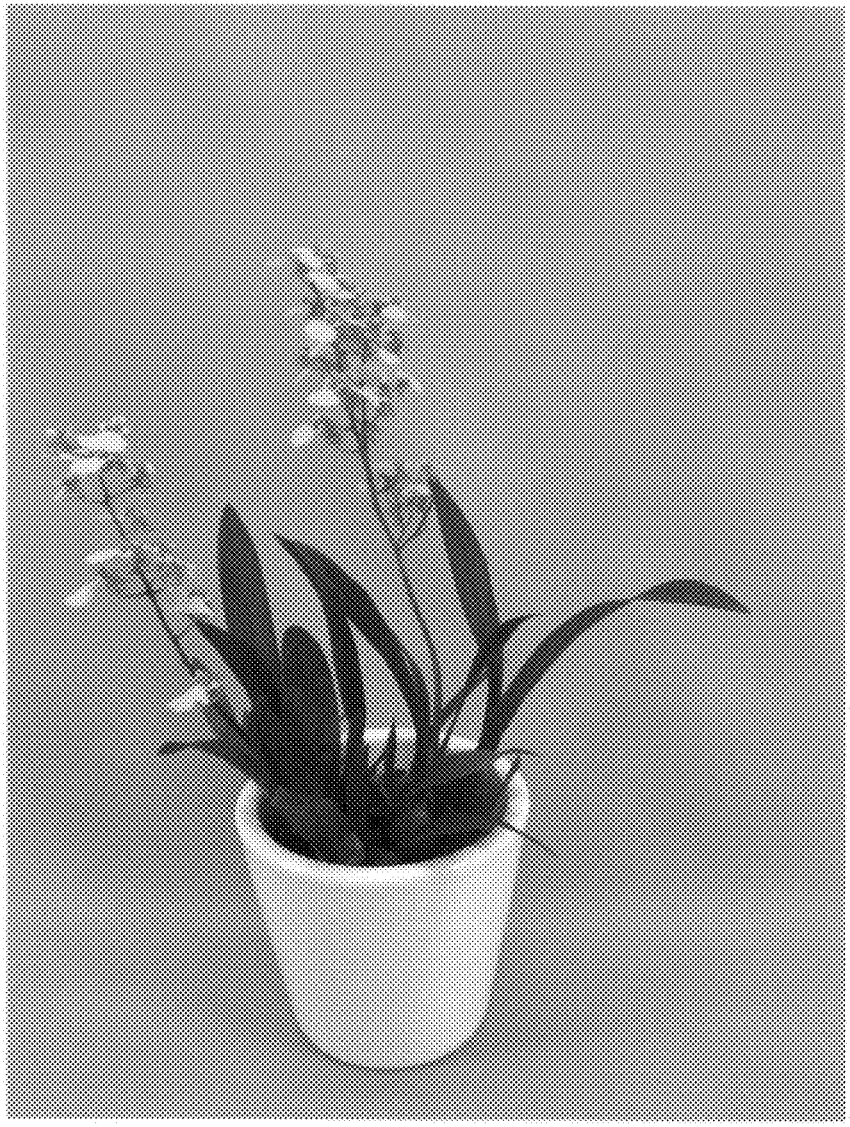
FIG. 1 shows the overall plant habit, including blooms and foliage of 'ONCDBALCOJ'.
Figure 2:
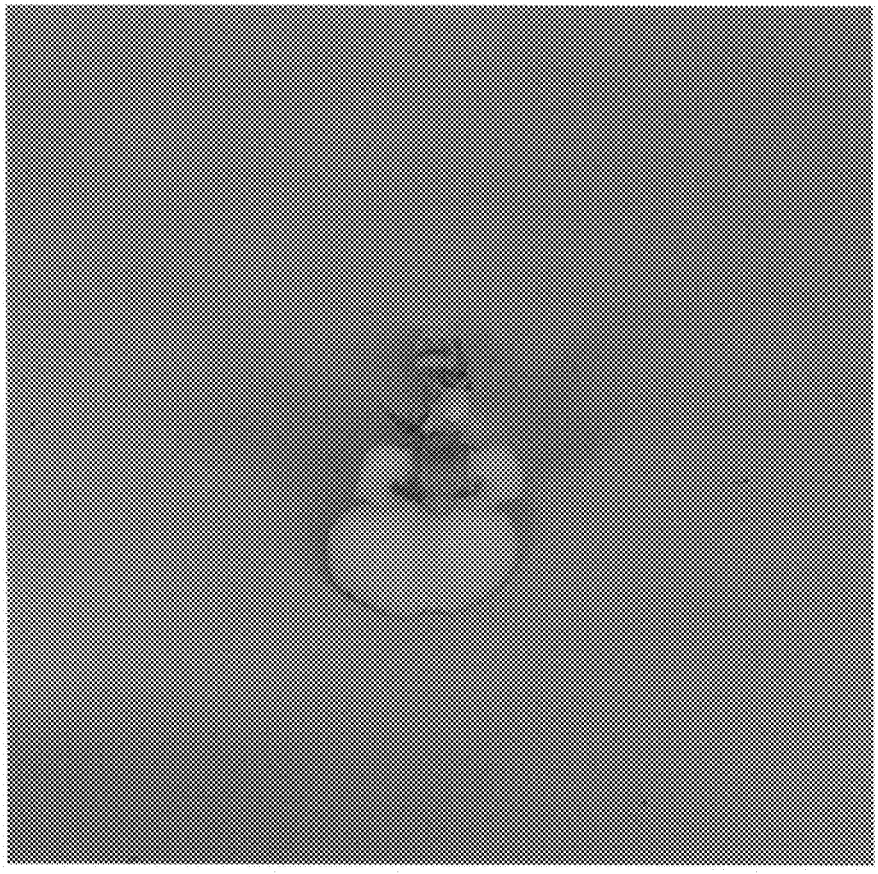
FIG. 2 shows a close-up of a flower of 'ONCDBALCOJ'.
Figure 3:
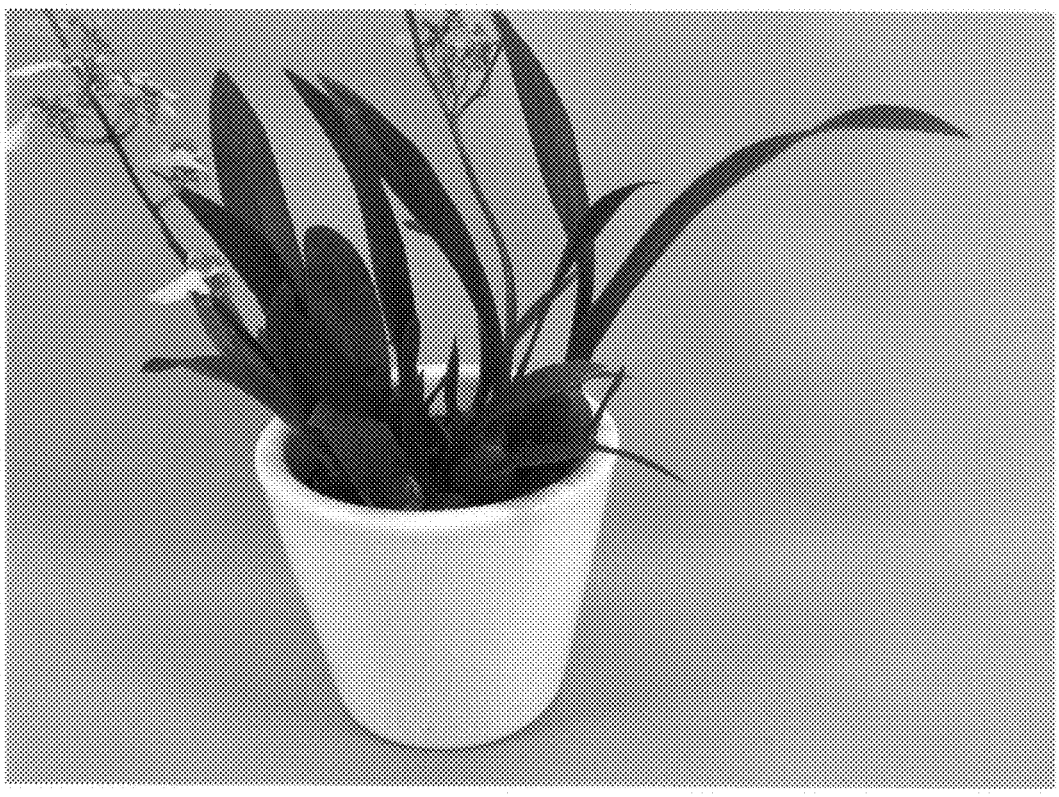
FIG. 3 shows a close-up of the leaves of 'ONCDBALCOJ'.

The following detailed description sets forth the distinctive characteristics of 'ONCDBALCOJ'. The data which define these characteristics were collected from asexual reproductions carried out in Bleiswijk, The Netherlands. The plant history was taken on 40-week old plants which were planted from tissue culture in 9 centimeter pots and grown in a greenhouse between 20° C. to 25° C. for 40 weeks. Observations were made in December 2014. Color readings were taken under 4-6000 lux natural light in the greenhouse. Color references are primarily to The R.H.S. Colour Chart of The Royal Horticultural Society of London (R.H.S.) (2001).

DETAILED BOTANICAL DESCRIPTION

Classification:
- *Family*.—Orchidaceae.
- *Botanical*.—*Oncidium altissimum* Sw.
- *Common name*.—*Oncidium*.
- *Variety name*.—'ONCDBALCOJ'.

Parentage:
- *Female parent*.—*Oncidium* cultivar '60000-0041' (unpatented).
- *Male parent*.—*Oncidium* cultivar '60000-0522' (unpatented).

Propagation:
- *Type*.—Tissue culture.

Plant:
- *Crop time* (*time to produce a finished flowering plant*).—20 to 40 weeks for a 9 cm pot.
- *Growth habit of peduncle*.—Sympodial.
- *Height* (*including pot, including inflorescence*).—25.0 cm to 35.0 cm.
- *Average plant spread*.—10.0 cm to 15.0 cm.
- *Vigor*.—Moderate.

Roots:
- *Root description*.—White colored roots with white, transparent growing tips (The exact shades of white may vary with minimal changes of environmental conditions).

Pseudobulb:
- *Shape*.—Laterally compressed ovoid.
- *Height*.—3.7 cm to 4.2 cm.
- *Length*.—2.8 cm to 3.3 cm.
- *Width*.—2.0 cm to 2.3 cm.
- *Color*.—Green (RHS 146A).

Leaves:
- *Mature leaves*.—Quantity per plant: 2 to 4 leaves are produced before flowering. Length (fully expanded): 8.5 cm to 9.5 cm. Width: 1.7 cm to 2.3 cm. Shape: Lanceolate. Base shape: Moderately elongated. Apex: Acute. Leaf margin: Entire. Color: Upper surface: RHS 146A. Lower surface: RHS 146B. Texture: Upper surface: Smooth. Lower surface: Slightly rough. Thickness: 0.70 mm to 0.80 mm. Venation: Pattern: Parallel. Color of the midvein: Upper surface: RHS 146A. Lower surface: RHS 146B.

Peduncle:
- *Quantity per plant*.—1 to 3.
- *Number of flowers per peduncle*.—15 to 45 (number of flowers depends on the branching of the inflorescence).
- *Length*.—18.0 cm to 23.0 cm.
- *Diameter*.—2.0 mm to 3.0 mm.
- *Strength*.—Moderate.
- *Aspect*.—Upright.
- *Texture*.—Smooth.
- *Color*.—Green (RHS 146B).
- *Internode length*.—12.0 mm to 22.0 mm.
- *Number of branches*.—0 to 4.

Inflorescence description:
- *Appearance*.—Upright, raceme to panicle inflorescence with bilaterally symmetrical flowers that open in succession beginning with the lowermost flower.
- *Inflorescence size*.—Height (from base to tip): 100.0 mm to 130.0 mm.
- *Flowering time*.—All year; first flowers can be expected 5 to 9 months after planting in a 9 cm pot.
- *Flower*.—Height: 19.0 mm to 24.0 mm. Diameter: 11.0 mm to 16.0 mm.
- *Flower longevity*.—On the plant: 5 to 10 weeks.
- *Fragrance*.—Present (Slight fragrance).
- *Petals*.—Shape: Ovate. Length (from base to tip): 6.0 mm to 9.0 mm. Width: 2.0 mm to 5.0 mm. Color (when fully opened): Upper surface: Basic color: Yellow (RHS 6C). Over color: Striped (RHS 172A). Lower surface: Basic color: Yellow (RHS 7D). Over color: Striped (RHS 172B).

*Dorsal sepal*.—Shape: Elliptic. Length (from base to tip): 5.0 mm to 8.0 mm. Width: 2.0 mm to 5.0 mm. Color (when fully opened): Upper surface: Basic color: Yellow (RHS 6C). Over color: Striped (RHS 172A). Lower surface: Basic color: Yellow (RHS 7D). Over color: Striped (RHS 172B).

*Lateral sepals*.—Shape: Ovate. Length (from base to tip): 6.0 mm to 9.0 mm. Width: 2.0 mm to 5.0 mm. Color (when fully opened): Upper surface: Basic color: Yellow (RHS 6C). Over color: Striped (RHS 172A). Lower surface: Basic color: Yellow (RHS 7D). Over color: Striped (RHS 172B).

*Labellum* (*lip*).—Length: 8.0 mm to 13.0 mm. Width: 14.0 mm to 19.0 mm.

*Lateral lobe*.—Color: Upper surface: Yellow (RHS 5B). Lower surface: Yellow (RHS 5C).

*Apical lobe*.—Color: Upper surface: Yellow (RHS 5B). Lower surface: Yellow (RHS 5C).

*Callus*.—Average size: Very small. Shape: Indescribable. Color: Greyed-orange (RHS 167A).

Reproductive organs:

*Arrangement*.—The stamens, style and stigmas are fused into a single, short structure called the column, possessing one terminal anther with pollen grains united into pollinia, which are covered by an anther cap. The stigma is located under the column behind the pollinia. The ovary is inferior with three carpels present.

*Column*.—Length: 3.0 mm to 4.0 mm. Diameter: 2.0 mm. Color: Green (RHS 143C). Color of wings of the column: Yellow (RHS 6C).

*Pollinia*.—Quantity: 2. Diameter: 0.2 mm to 0.3 mm. Color: Yellow-orange (RHS 22A).

*Ovary*.—Length: Not visible.

*Pedicel*.—Length: 16.0 mm to 18.0 mm. Diameter: 0.9 mm to 1.1 mm. Color: Green (RHS 144B) at the base and towards the flower; lighter green (RHS 144C) at the middle.

Disease, pest, and stress resistance: No specific resistance or susceptibility observed.

Temperature tolerance: Not observed.

COMPARISON WITH PARENTAL AND COMMERCIAL VARIETIES

'ONCDBALCOJ' differs from female parent '60000-0041' (unpatented) in that 'ONCDBALCOJ' has an acute leaf apex, whereas '60000-0041' has an unequal obtuse leaf apex. Additionally, 'ONCDBALCOJ' has a shorter plant with smaller flowers than '60000-0041'.

'ONCDBALCOJ' differs from male parent '60000-0522' (unpatented) in that 'ONCDBALCOJ' has an acute leaf apex and a smaller callus that is light brown, whereas '60000-0522' has an unequal obtuse leaf apex and a larger callus that is darker brown. Additionally, 'ONCDBALCOJ' has a larger flower than '60000-0522'.

'ONCDBALCOJ' differs from commercial variety 'SWEET SUGAR' (unpatented) in that 'ONCDBALCOJ' has a smaller lip, a smaller pseudobulb and smaller pollinia than 'SWEET SUGAR'.

I claim:

1. A new and distinct variety of *Oncidium* plant named 'ONCDBALCOJ', substantially as described and illustrated herein.

* * * * *